United States Patent [19]

Gard

[11] Patent Number: 4,946,662

[45] Date of Patent: Aug. 7, 1990

[54] METHOD OF FORMING CONDENSED PHOSPHATES IN AQUEOUS SOLUTIONS

[75] Inventor: David R. Gard, Ballwin, Mo.

[73] Assignee: Monsanto Company, St. Louis, Mo.

[21] Appl. No.: 374,407

[22] Filed: Jun. 30, 1989

[51] Int. Cl.$^5$ .................... C01B 15/16; C01B 25/26
[52] U.S. Cl. ................................. 423/314; 423/305; 423/315
[58] Field of Search ............ 423/302, 314, 315, 299, 423/305

[56] References Cited

U.S. PATENT DOCUMENTS

| | | | |
|---|---|---|---|
| 3,157,465 | 11/1964 | Nielsen | 423/302 |
| 3,236,592 | 2/1966 | Nielsen | 423/302 |
| 3,367,737 | 2/1968 | Moore et al. | 23/106 |
| 3,382,037 | 5/1965 | Shaffery et al. | 23/106 |
| 3,393,974 | 7/1968 | Rohlfs et al. | 423/314 |

OTHER PUBLICATIONS

Clark et al., J. Chem. Soc. 1969, 233.
Griffith et al., J. Amer. Chem. Soc., 89, 2884 (1967).
Quimby et al., J. Amer. Chem. Soc., 82, 1099 (1960).
Kosolaphoff, Organophosphorus Cmpds, John Wiley and Sons NY, 1950, Chap. 12.

*Primary Examiner*—Gregory A. Heller
*Attorney, Agent, or Firm*—Linda L. Lewis; Raymond C. Loyer; Arnold H. Cole

[57] ABSTRACT

A method of forming condensed phosphates comprising reacting phosphate ions, such as generated from polyphosphate salts, and sulfamides, in an aqueous solution or suspension. An example of such a reaction is the reaction of tetrasodium tripolyphosphate and sulfamide in water to form sodium trimetaphosphate.

11 Claims, No Drawings

METHOD OF FORMING CONDENSED PHOSPHATES IN AQUEOUS SOLUTIONS

BACKGROUND OF THE INVENTION

This invention relates to a method of forming condensed phosphates and amidophosphates in an aqueous solution. More specifically, this invention relates to a method of forming condensed phosphates, such as sodium trimetaphosphate, and amidophosphates in an aqueous solution or suspension using sulfamides and phosphate ions.

Condensed phosphates are characterized by the presence of at least one P—O—P linkage which is formed by the dehydration of orthophosphates or the dehydration of less highly condensed phosphates. Condensed phosphates are typically made in industry by heating orthophosphates to very high temperatures to drive off water of constitution. U.S. Pat. No. 3,367,737 discloses a method of manufacturing an alkali metal polyphosphate, such as sodium trimetaphosphate, by calcining an inorganic alkali metal phosphate, such as monosodium orthophosphate, at a temperature of from about 450° to 620° C. U.S. Pat. No. 3,382,037 discloses a method to produce sodium trimetaphosphate by continuously feeding an aqueous solution of sodium phosphate through a reaction zone while introducing combustion gases at a temperature of from about 800° to 850° C.

The condensation of phosphates is also chemically effected. V. M. Clark, et. al., J. Chem. Soc. (C), 1969, 233, disclose a method of chemically dehydrating phosphates with reagents such as chloroquinones to form condensed phosphates. Chemical dehydrations of this type are extremely sensitive to traces of moisture and sufficient water completely inhibits the reaction E. J. Griffith, et. al., J. Amer. Chem. Soc., 89, 2884 (1967), disclose rearrangements of condensed phosphates in aqueous solution, such as the formation of cyclic trimetaphosphate from hexaphosphate. Although one new P—O—P linkage is formed, it is at the expense of another with no net change in the degree of condensation.

Typically, the formation of amidophosphates requires anhydrous conditions. G. M. Kosolapoff, Organophosphorus Compounds, John Wiley and Sons, 1950. 293, discloses the reaction of triethyl phosphate and ammonia in ether or alcohol to form diethylamidophosphate. Also the reactions of secondary phosphites with primary or secondary amines in the presence of aliphatic polyhalide to from amidophosphates are disclosed. D. E. C. Corbridge, Phosphorous, An Outline of its Chemistry, Biochemistry and Technology, Third Edition, Elsevier, 1985, 291, discloses the reaction of ammonia with phenyl phosphodichlorides to form amidophosphates. O. T. Quimby, et.al., Z. Anorg. Allg. Chem., 296, 224(1958), disclose that small cyclic phosphates, such as trimetaphosphate, are an exception to the requisite anhydrous conditions, and react with aqueous ammonia to form monoamidotriphosphate.

Derivatized phosphates are known to form condensed phosphates under controlled hydrolytic conditions. O. T. Quimby, et. al., J. Amer. Chem. Soc., 82, 1099 (1960), disclose the condensation of amidophosphates in aqueous media to form condensed phosphates. G. M. Kosolaphoff, Organophosphorus Compounds, John Wiley and Sons, Inc., New York, 1950, Chap. 12, discloses condensation reactions using halophosphates and/or phosphate esters.

None of the above references disclose a method preparing condensed phosphates and amidophoshates in an aqueous solution from sulfamides and phosphate ions.

SUMMARY OF THE INVENTION

The present invention is a method of forming condensed phosphates and amidophosphates in an aqueous solution using sulfamides and phosphate ions.

DETAILED DESCRIPTION OF THE INVENTION

The present invention provides a method of forming condensed phosphates and amidophosphates in an aqueous solution using sulfamides and phosphate ions. The phosphate ions are of the formula

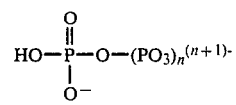

where n is from about 1 to about 1000. A preferred range for n is from about 1 to about 10. The phosphate ions may be generated from such phosphate salts as sodium tripolyphosphate, sodium phenylorthophosphate, tetrasodium pyrophosphate, tetrapotassium pyrophosphate, ammonium tetrapolyphosphate and potassium tripolyphosphate, which upon dissolution in the appropriate pH range, e.g., about 8 to about 10, generate the desired phosphate ions. Unsubstituted orthophosphate ions or a disubstituted phosphate ion will not form condensed phosphates or amidophosphates with the present method.

The present invention, in addition to producing condensed phosphates and amidophosphates, produces hydrolysis products such as orthophosphate, pyrophosphate, ammonium, imidodisulfamide and sulfamate ions. However, the formation of condensed phosphates may be greater than the loss to hydrolysis i.e., there may be a net gain in condensed phosphates. The type of condensed phosphates formed depends on the phosphate ion starting material. If polyphosphates of the above formula are used where n is 2 or greater, such as sodium tripolyphosphate, trimetaphosphate is formed. Various amidophosphates, such as amidodiphosphate and amidotriphosphate, may also be formed. When n is 1, i.e., pyrophosphate, the condensation product is an amidophosphate, formed by condensation of the phosphate ion with the sulfamide. Various other condensation products may also be formed, such as trimetaphosphate and tripolyphosphate. If orthophosphate or diphenyl phosphoric acid is the starting material, no reaction is observed.

The sulfamide suitable for use in the present invention is of the following formula

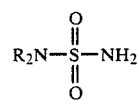

where R is alkyl, aryl, substituted alkyl or substituted aryl, hydrogen or a combination thereof. Examples of such substituents include methyl, ethyl, propyl, butyl, phenyl or benzyl. It is necessary that one or both of the amino groups be unsubstituted for the sulfamide to be effective in this invention. Examples of suitable sulfamides include sulfamide, methyl sulfamide, N,N-dimethyl sulfamide, butyl sulfamide, N,N-diethyl sulfamide and imidodisulfamide. Compounds of some structural similarity to the above sulfamides, and sulfamides that are substituted on both amino groups are ineffective in this method to produce condensed phosphates. Examples of ineffective compounds are sulfamic acid, methane sulfonamide, p-toluene sulfonamide, sulfanilamide, urea, benzyl carbamate, formamide, N,N'-dimethyl sulfamide, succinimide, diacetamide, ammonium carbamate and 2,2,2-trichloroacetamide. Biuret and urethan yield trace amounts of trimetaphosphate.

Typically, the concentration of the sulfamide in the reaction mass is not critical. The mole ratio of phosphate starting material to sulfamide can vary in the range of from about 5 to about 0.001. A preferred range is from about 3 to about 1. For some reactions, such as the reaction of N,N-dimethyl sulfamide with pyrophosphate, the mole ratio must be less than about 5 to effect substantial reaction.

The condensation reaction occurs in an aqueous solvent suitable to dissolve or suspend the phosphate and sulfamide to provide intimate mixing. A preferred solvent is an aqueous polar solvent that will dissolve or suspend the phosphate to provide intimate mixing. Examples include water, mixtures of water and dimethylsulfoxide, of water and a ketone or of water and an alcohol. Examples include water and acetone, water and methanol or water and isopropyl alcohol. A preferred solvent is water. The concentration of phosphate starting material in the solvent is not critical. The concentration can vary in the range of from 1 to 50 weight %. A preferred range is from 1 to 35 weight %.

The pH of the reaction mass is critical and should be in the range of about 8 to about 10. When the pH is higher or lower, the reaction is significantly diminished or does not occur. For some reactions, such as with butyl sulfamide or N,N-dimethylsulfamide and pyrophospate, the pH range is narrower, in the range of about 9 to 10.

The reaction temperature is not critical and can vary from about 0° C. to about 100° C., or the boiling temperature of the solvent. Typically, at higher temperatures, the reaction rate is higher and, subsequently, the yields are higher for the same reaction time. A preferred temperature is from about 30° to 100° C.

The reaction time is not critical and can vary from about 1 to 600 h. Typically, the yield of condensed phosphates increases with time, however, after about 315 h., the yield decreases. A preferred range of reaction time is from about 2 to 300 h.

The following examples are intended to illustrate the present invention and are not to limit the claims in any manner. All of the percentages are by weight unless otherwise indicated.

EXAMPLES

The following examples were prepared as follows: The sulfamide or additive and phosphate salts to generate the phosphate ions were placed in a test tube and sufficient water added to bring the volume to 12 ml. The pH was adjusted by the addition of acid such as hydrochloric or sulfuric acid or by the addition of base such as sodium hydroxide. Concentrated acids or base were used to maintain approximately a constant volume of 12 ml. The test tube was capped and placed in a constant temperature bath. The pH was periodically checked (every 1 to 3 days) to maintain an approximately constant value ($\pm 0.2$ units) over the course of the reaction. The sample was quantitatively analyzed by P-31 NMR and the results reported as yield (mole %) phosphorus of the product determined by the total moles of phosphorus in the sample.

Controls C-1 through C-9 and examples 1 through 7, shown in Table I, demonstrate the effect of varying the pH of the reaction. The phosphate used was sodium tripolyphosphate (1.9 weight %), the additive used was sulfamide and the reaction temperature was 60° C. The P-31 NMR analysis were coded as follows: T was trimetaphosphate anion, TP was tripolyphosphate anion, NP3 was amidotriphosphate, NP2 was amidodiphosphate and BuNP2 was N-butylamidodiphosphate. As can be seen by the data below, the effective pH range was from about 8 to about 10. In the absence of sulfamide, no reaction was detected.

TABLE I

Varying the pH of the Samples

| Example | Sulfamide (%) | pH | Time (h.) | Yield (mole %) |
|---|---|---|---|---|
| C-1 | 0 | 5 | 48 | 0 |
| C-2 | 0 | 7 | 48 | 0 |
| C-3 | 0 | 8 | 136 | 0 |
| C-4 | 0 | 9 | 143 | 0 |
| C-5 | 0 | 10 | 354 | 0 |
| C-6 | 2 | 5 | 48 | 0 |
| C-7 | 2 | 7 | 48 | 0 |
| 1 | 2 | 8 | 73 | 13, T |
| 2 | 2 | 8 | 136 | 18, T |
| 3 | 2 | 8 | 184 | 20, T |
| 4 | 2 | 9 | 263 | 18, T |
| 5 | 2 | 10 | 142 | 3, T<br>1, NP2<br>9, NP3 |
| 6 | 2 | 10 | 315 | 4, T |
| 7 | 2 | 10 | 354 | 1, T<br>3, NP2<br>5, NP3 |
| C-8 | 2 | 11 | 330 | 0 |
| C-9 | 2 | 12 | 330 | 0 |

Examples 8 through 14 and control 10, shown in Table II, illustrate the effect of varying pH and reaction time. The phosphate used was tetrasodium pyrophosphate (2 weight %, except for example 14 which used 5 weight %), the reaction temperature was 60°, and the additive used was sulfamide (2 weight %, except for example 14 which used 5 weight %). The yield increased with time up to about 315 h., then decreased (see examples 12 and 13). At a pH above 10, no reaction was observed (see C-10).

TABLE II

Varying the pH and Reaction Time of the Samples

| Example | pH | Time (h.) | Yield (mole %) |
|---|---|---|---|
| 8 | 8 | 138 | 6, NP2 |
| 9 | 8 | 263 | 15, NP2 |
| 10 | 9 | 145 | 10, NP2 |
| 11 | 10 | 142 | 21, NP2 |
| 12 | 10 | 315 | 43, NP2 |
| 13 | 10 | 354 | 20, NP2 |
| C-10 | 12 | 330 | 0 |
| 14 | 10 | 259 | 22, NP2 |

Examples 15 through 22, shown in Table III, illustrate the effect of varying the solvent and pH of the reaction mass. The additive used was sulfamide (2.0 weight %), the phosphate used was tetrasodium pyrophosphate (2.0 weight %), the reaction temperature was 60° C., and the reaction time was 168 h. For the examples run in water (15 through 18), increasing the pH from 9.8 to 10.6 resulted in a decrease in amidophosphate yield. Adding tetramethyl ammonium chloride resulted in an increases in amidophosphate yield at the same or similar pH (see examples 17, 20 and 21). The addition of ammonia or sodium chloride had a small adverse effect on yield (see examples 17, 19 and 22).

TABLE III

Varying the Solvent and pH of the Samples

| Example | Solvent (molar) | pH | Yield (mole %) |
|---|---|---|---|
| 15 | water | 9.8 | 17, NP2 |
| 16 | water | 10.2 | 10, NP2 |
| 17 | water | 10.4 | 7, NP2 |
| 18 | water | 10.6 | 3, NP2 |
| 19 | 0.2 ammonia | 10.4 | 5, NP2 |
| 20 | 0.2 tetramethyl ammonium chloride | 10.4 | 11, NP2 |
| 21 | 0.5 tetramethyl ammonium chloride | 10.5 | 14, NP2 |
| 22 | 0.2 sodium chloride | 10.3 | 5, NP2 |

Controls C-11 through C-20, shown in Table IV, illustrate the effect of varying the pH and the phosphate starting material. The additive used was sulfamide (2.0 weight %), and the reaction temperature was 60° C. No reaction was observed using orthophosphate or diphenyl phosphoric acid starting material, regardless of pH (see C-11 through C20).

TABLE IV

Varying the pH and Phosphate

| Example | Phosphate (weight %) | pH | Time (h.) | Yield (mole %) |
|---|---|---|---|---|
| C-11 | ortho, 2.0 | 7 | 150 | 0 |
| C-12 | ortho, 2.0 | 8 | 142 | 0 |
| C-13 | " | 8 | 150 | 0 |
| C-14 | " | 9 | 145 | 0 |
| C-15 | " | 10 | 142 | 0 |
| C-16 | " | 10 | 150 | 0 |
| C-17 | " | 11 | 150 | 0 |
| C-18 | " | 12 | 150 | 0 |
| C-19 | diphenyl phosphoric acid, 2.0 | 8 | 142 | 0 |
| C-20 | diphenyl phosphoric acid, 2.0 | 10 | 142 | 0 |

Examples 23 through 35 and controls C-21 through C-28, shown in Table V, illustrate the effect of varying the sulfamide additive, the phosphate starting material, the pH and the reaction time. The reaction temperature was 60° C. For butyl sulfamide and N,N-dimethyl sulfamide reactions with pyrophosphate, it appears that pH 8 is too low to effect a net reaction to yield an amidophosphate (see C-21, C-22 and C-23). For the N,N-dimethyl sulfamide reaction with pyrophosphate, it appears that 0.5 % sulfamide is inadequate to effect a substantial net reaction (see C-24 and C-25). The disubstituted N,N'-dimethyl sulfamide is an ineffective reactant for this system (see C-26, C-27 and C-28). Butyl sulfamide, N.N-dimethylsulfamide and imidodisulfamide (at proper pH and concentration) are effective in producing condensed phosphates or amidophosphates.

TABLE V

Varying the Sulfamide, the Phosphate, the pH and the Reaction Time

| Example | Sulfamide (%) | Sodium Phosphate (%) | pH | Time (h.) | Yield (molar) |
|---|---|---|---|---|---|
| 23 | butyl, 4.6 | tripoly, 1.9 | 9 | 143 | 7, T |
| 24 | butyl, 2.0 | tripoly, 1.9 | 8 | 142 | 1, T |
| 25 | butyl, 2.0 | tripoly, 1.9 | 10 | 142 | 4, T |
| C-21 | butyl, 2.0 | pyro, 2.0 | 8 | 142 | 0 |
| 26 | butyl, 2.0 | pyro, 2.0 | 10 | 142 | 5, BuNP2 |
| C-22 | butyl, 0.5 | pyro, 8.0 | 8 | 70 | 0 |
| 27 | butyl, 0.5 | pyro, 8.0 | 10 | 70 | 0.1 BuNP2 |
| 28 | N,N-dimethyl, 0.5 | tripoly, 1.9 | 8 | 142 | 1, T |
| 29 | N,N-dimethyl, 0.5 | tripoly, 1.9 | 9 | 142 | 4, T |
| C-23 | N,N-dimethyl, 2.0 | pyro, 2.0 | 8 | 142 | 0 |
| 30 | N,N-dimethyl, 2.0 | pyro, 2.0 | 9 | 142 | 2, NP2 |
| 31 | N,N-dimethyl, 2.0 | pyro, 2.0 | 10 | 142 | 4, NP2 |
| C-24 | N,N-dimethyl, 0.5 | pyro, 8.0 | 8 | 70 | 0 |
| C-25 | N,N-dimethyl, 0.5 | pyro, 8.0 | 10 | 70 | 0 |
| C-26 | N,N'-dimethyl, 2.0 | tripoly, 1.9 | 9 | 142 | 0 |
| C-27 | N,N'-dimethyl, 2.0 | tripoly, 1.9 | 9 | 142 | 0 |
| C-28 | N,N'-dimethyl, 2.0 | pyro, 2.0 | 9 | 142 | 0 |
| 32 | Imidodi, 1.6 | tripoly, 1.9 | 9 | 142 | 7, T |
| 33 | " | tripoly, 1.9 | 10 | 142 | 1, NP2 |
| 34 | " | pyro, 2.0 | 9 | 142 | 4, NP2 |
| 35 | " | pyro, 2.0 | 10 | 142 | 3, NP2 |

Controls C-29 through C-34, shown in Table VI, show the effect of varying the type of sulfamide/additive on the yield. The reaction pH was 9, and the reaction temperature was 60° C. No reaction was observed using sulfamic acid, methanesulfamide, p-toluenesulfonamide and sulfonamide (see C-29 through C-34).

TABLE VI

Varying the Sulfamide

| Example | Sulfamide/ Additive (%) | Sodium Phosphate (%) | Time (h.) | Yield (mole %) |
|---|---|---|---|---|
| C-29 | Sulfamic acid, 2.0 | tripoly, 1.9 | 118 | 0 |
| C-30 | Sulfamic acid 2.0 | pyro, 2.0 | 118 | 0 |
| C-31 | Sulfamic acid 2.0 | ortho, 2.0 | 118 | 0 |
| C-32 | methanesulfon- amide, 2.0 | tripoly, 1.9 | 212 | 0 |
| C-33 | p-toluene- sulfonamide, 4.6 | tripoly, 1.9 and 17% ethanol | 212 | 0 |
| C-34 | Sulfanilamide, | tripoly, 1.9 | 212 | 0 |

Controls C-35 through C-49, shown in Table VII, show the effect of using additives that are amino derivatives of carbon dioxide and carboxylic acids. The phosphate starting material was sodium tripolyphosphate, with the exception of C-43 and C-45 which used tetrasodium pyrophosphate, and the reaction temperature was 60° C. No reaction was observed for controls using urea, benzyl carbamate, formamide, succinimide, diacetamide, ammonium carbamate and 2,2,2-trichloroacetamide. Trace amounts (<1%) of trimetaphosphate were formed using biuret and urethan.

TABLE VIII

| | Varying the Additive | | | | |
|---|---|---|---|---|---|
| Example | Additive (%) | Sodium Phosphate (%) | pH | Time (h.) | Yield (mole %) |
| C-35 | Urea, 2.0 | 1.9 | 9 | 212 | 0 |
| C-36 | Urea, 10 | 3.4 | 9 | 142 | 0 |
| C-37 | Biuret, 3.0 | 1.9 | 9 | 143 | 0.5, T |
| C-38 | Biuret, 10 | 3.4 | 9 | 142 | 0.5, T |
| C-39 | Urethan, 2.7 | 1.9 | 9 | 143 | 0.4, T |
| C-40 | Urethan, 10 | 3.4 | 9 | 142 | 0.1, T |
| C-41 | Benzyl Carbamate, 4.5 | 1.9 | 9 | 143 | 0 |
| C-42 | Formamide, 2.0 | 1.9 | 9 | 142 | 0 |
| C-43 | Formamide, 2.0 | 2.0 | 9 | 142 | 0 |
| C-44 | Succinimide, 2.0 | 1.9 | 8 | 142 | 0 |
| C-45 | Succinimide, 2.0 | 2.0 | 8 | 142 | 0 |
| C-46 | Diacetamide, 0.3M | 1.9 | 9 | 143 | 0 |
| C-47 | Ammonium Carbamate, 0.3M | 1.9 | 9 | 143 | 0 |
| C-48 | Carbamate, 10 | 3.4 | 9 | 142 | 0 |
| C-49 | 2,2,2-trichloroacetamide, 4,2, in 17% ethanol | 1.9 | 9 | 212 | 0 |

Examples 36 through 41, shown in Table VIII, illustrate the effect of varying the reaction temperature and the concentration of the reactants. The additive was sulfamide (2%), and the pH was 9 (except for example 40, which was 17% sulfamide and pH 9.2). Typically, increasing the temperature from 60° C. to 80° C. increased the reaction rate and the yield (see examples 36 and 10). Likewise, decreasing the reaction temperature from 60° C. to 25° C., decreased the reaction rate and yield (see examples 37 and 10). Increasing the concentration of the reactants at the reaction temperature of 60° C., increased the reaction rate and the yield of NP2 (see examples 40 and 10).

TABLE VIII

| | Varying the Reaction Temperature and Concentration of Reactants | | | |
|---|---|---|---|---|
| Example | Phosphate (Weight %) | Temperature (°C.) | Time (h.) | Yield (mole %) |
| 36 | pyro, 2 | 80 | 25 | 21, NP2 |
| 37 | pyro, 2 | 25 | 696 | <2, NP2 |
| 38 | tripoly, 2 | 80 | 25 | 21, T |
| 39 | tripoly, 2 | 25 | 696 | 2, T |
| 40 | pyro, 29 | 60 | 90 | 4, TP 1, T 36, NP2 |
| 41 | tetrapoly, 3 | 60 | 72 | 34, TP 2, T |

I claim:

1. A method of forming an aqueous solution of suspension of condensed phosphates comprising reacting together sulfamides and phosphate ions in an aqueous solution or mixture at a pH of from about 8 to 10, whereby the aqueous solution or suspension of condensed phosphates is formed.

2. The method of claim 1 wherein the phosphate ions are of the formula

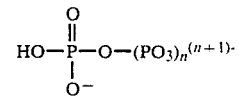

where n is from about 1 to about 1000.

3. The method of claim 2 wherein the phosphate ions are generated from phosphate salts selected from the group consisting of sodium tripolyphosphate, sodium phenylorthophosphate, ammonium tetrapolyphosphate and potassium tripolyphosphate.

4. The method of claim 2 wherein the sulfamide is of the following formula

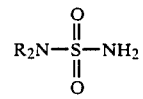

where R is alkyl, aryl, substituted alkyl or substituted aryl, hydrogen or a combination thereof.

5. The method of claim 4 wherein the sulfamide is selected from the group consisting of sulfamide, methyl sulfamide N,N-dimethyl sulfamide, butyl sulfamide, N,N-diethyl sulfamide and imidodisulfamide.

6. The method of claim 4 wherein the aqueous solution is made with an aqueous polar solvent that will dissolve or suspend the phosphate to provide intimate mixing.

7. The method of claim 6 wherein the aqueous polar solvent is selected from the group consisting of water, mixtures of water and dimethylsulfoxide, mixtures of water and a ketone, and mixtures of water and an alcohol.

8. The method of claim 6 wherein the aqueous polar solvent is water.

9. The method of claim 8 wherein the reaction temperature is from about 30° C. to about 100° C.

10. The method of claim 9 wherein the reaction time is from about 2 to 300 h.

11. A method of forming an aqueous solution of suspension of condensed phosphates comprising reacting together a sulfamide of the formula

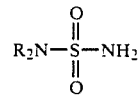

where each R is independently selected from the group consisting of alkyl, aryl, substituted alkyl or substituted aryl, hydrogen or a combination thereof, and phosphate ions of the formula

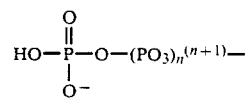

where n is from about 2 to about 1000, in an aqueous polar solvent selected from the group consisting of water, mixtures of water and dimethlysulfoxide, mixtures of water and a ketone and mixtures of water and an alcohol, at a pH in the range of from about 8 to about 10, at a reaction temperature of from about 30° C. to about 100° C., and at a reaction time of from about 2 h to 300 h.

* * * * *